United States Patent [19]
Zanini-Fisher et al.

[11] Patent Number: 5,863,803
[45] Date of Patent: Jan. 26, 1999

[54] METHOD AND APPARATUS FOR MODULATING A GAS SAMPLE FOR A CALORIMETRIC GAS SENSOR

[75] Inventors: Margherita Zanini-Fisher, Bloomfield Hills; Jacobus H. Visser, Farmington; E. M. Logothetis, Birmingham, all of Mich.

[73] Assignee: Ford Global Technologies, Inc., Dearborn, Mich.

[21] Appl. No.: 772,661

[22] Filed: Dec. 20, 1996

[51] Int. Cl.$^6$ .................................................. G01N 25/32
[52] U.S. Cl. .......................... 436/147; 436/152; 422/51; 422/95
[58] Field of Search .................. 422/94, 95, 96, 422/97, 98, 51; 436/147, 152

[56] References Cited

U.S. PATENT DOCUMENTS

| | | |
|---|---|---|
| 4,542,640 | 9/1985 | Clifford . |
| 4,627,269 | 12/1986 | Forster et al. . |
| 4,833,909 | 5/1989 | Matthiessen .............................. 73/23 |
| 5,265,417 | 11/1993 | Visser et al. . |
| 5,451,371 | 9/1995 | Zanini-Fisher et al. . |
| 5,486,336 | 1/1996 | Dalla Betta et al. ...................... 422/90 |
| 5,527,446 | 6/1996 | Kosek et al. . |

FOREIGN PATENT DOCUMENTS 9300581  1/1993  WIPO .

*Primary Examiner*—Jeffrey Snay
*Attorney, Agent, or Firm*—Lorraine S. Melotik

[57] ABSTRACT

A method and apparatus is provided for modulating flux of combustibles reacting with oxygen impinging on a calorimetric gas sensor. The method includes the steps of enclosing a sensing element and a reference element of a calorimetric gas sensor with an apparatus having at least one aperture to allow combustibles to enter and impinge on the sensing element and reference element, periodically restricting the aperture of the apparatus to modulate the flux of combustibles entering at a predetermined frequency to produce an AC output signal from the calorimetric gas sensor, and measuring the sensor output at the frequency at which the aperture is restricted.

20 Claims, 2 Drawing Sheets

METHOD AND APPARATUS FOR MODULATING A GAS SAMPLE FOR A CALORIMETRIC GAS SENSOR

BACKGROUND OF THE INVENTION

1. Field of the Invention

The present invention relates generally to calorimetric devices and, more specifically, to a method and apparatus for modulating the flux of combustibles reacting with oxygen impinging on a calorimetric gas sensor.

2. Description of the Related Art

Federal and state regulations require motor vehicles to have on-board diagnostics (OBD II) to monitor the performance of emission related components. One of the OBD II functions is to monitor the hydrocarbon (HC) conversion efficiency of a three way catalyst (TWC). Currently, this function is accomplished by using a dual oxygen sensor method. By comparing the outputs of two exhaust gas oxygen sensors, one placed upstream and the other downstream of the catalytic converter, a measure of the oxygen storage capacity is obtained, which then must be related to the hydrocarbon conversion efficiency. Although this method is presently used in production vehicles, it suffers from the disadvantage of not being sufficiently robust. The reason is that the oxygen storage capacity of the TWC has a weak relationship to the catalytic converter HC efficiency which is the desired information. Furthermore, the applicability of the dual oxygen sensor method is even more questionable for ultra low emission vehicles (ULEV) where a) a major contribution to the HC emissions comes during cold start when the HEGO sensor is not operational and b) a few percent decrease in the HC efficiency of the TWC can cause emissions above the standards. Thus, there is a need in the art for a method for monitoring the HC efficiency of the catalytic convertor directly.

One method for monitoring the HC efficiency of the catalytic convertor is to use a HC sensor to measure directly tailpipe HC emissions. One example of a HC sensor is a calorimetric gas sensor as disclosed in U.S. Pat. No. 5,451, 371 to Zanini-Fisher et-al. Because of generally low concentrations of tailpipe HC in the ULEV, HC sensors must have a very low concentration detection limit and high stability. The stability of the calorimetric gas sensor is affected by zero-offset drifts. Also, when the calorimetric gas sensor is placed in the exhaust gas, the signal noise increases because the temperature fluctuations in the exhaust environment are not completely compensated by the differential nature of the sensor. Therefore, there is a need in the art to provide a method for improving the accuracy and detection limit of a calorimetric gas sensor.

SUMMARY OF THE INVENTION

Accordingly, the present invention is a method and apparatus for modulating the flux of combustibles reacting with oxygen impinging on a calorimetric gas sensor. The method includes the step of enclosing the sensing element and the reference element of a calorimetric gas sensor with an apparatus having at least one aperture to allow combustibles to enter and impinge on the sensing element and reference element. The method also includes [th]e step of periodically restricting the aperture of the apparatus to modulate the flux of combustibles entering into it at a predetermined frequency to produce an alternating current (AC) output signal from the calorimetric gas sensor and measuring the sensor output at the frequency at which the aperture is restricted.

One feature of the present invention is that the method and apparatus modulate the flux of combustibles reacting with oxygen to derive an AC output from a calorimetric gas sensor. Another feature of the present invention is that a method and apparatus are provided for modulating the flux of combustibles reacting with oxygen impinging on a calorimetric gas sensor so that the sensor output is measured at the frequency of modulation using frequency or phase-sensitive detection techniques to improve the accuracy and detection limit of the sensor. Yet another feature of the present invention is that the method and apparatus improve the detection limit of the calorimetric gas sensor so that it can be used in an environment with large thermal fluctuations. Still another feature of the present invention is that the method and apparatus eliminate the inaccuracy of the calorimetric gas sensor associated with drifts in the direct current (DC) zero-offset.

Other features and advantages of the present invention will be readily appreciated as the same becomes better understood after reading the subsequent description when considered in connection with the accompanying drawings.

DESCRIPTION OF THE PREFERRED EMBODIMENT(S)

Figure 1:
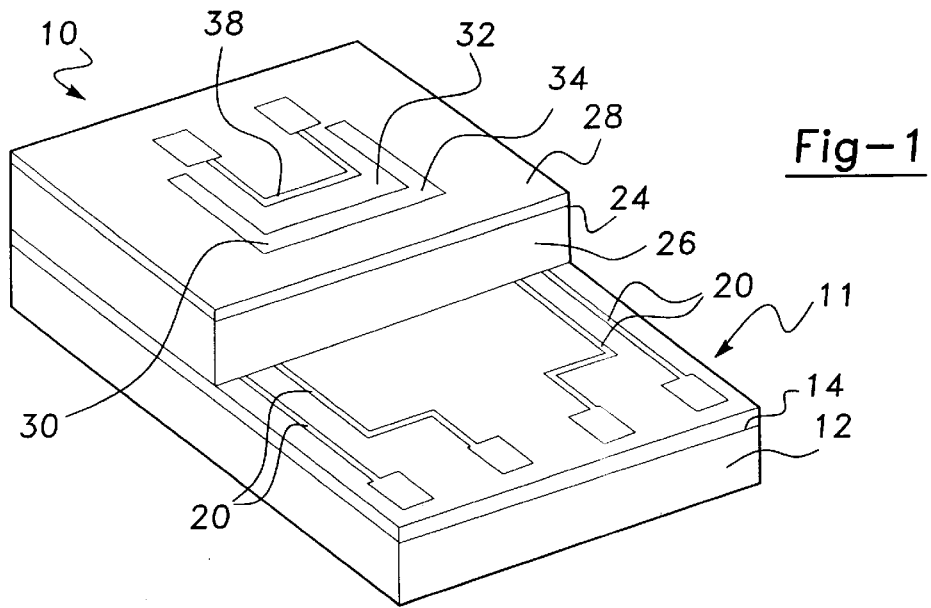
FIG. 1 is a perspective view of an apparatus, according to the present invention, illustrated in operational relationship with a calorimetric gas sensor.
Figure 2:
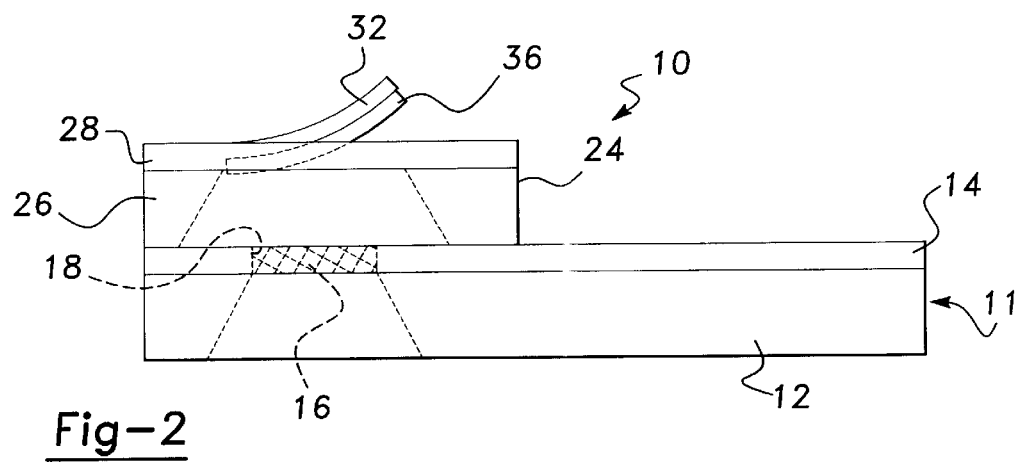
FIG. 2 is a cross-sectional view of the apparatus and calorimetric gas sensor of FIG. 1.

Referring to the drawings and in particular FIGS. 1 and 2, one embodiment of an apparatus 10, according to the present invention, is illustrated in operational relationship with a calorimetric gas sensor, generally indicated at 11. The calorimetric gas sensor 11 is preferably of a type disclosed in U.S. Pat. No. 5,451,371 to Zanini-Fisher et al, the disclosure of which is hereby incorporated by reference.

The calorimetric gas sensor 11 includes a bulk silicon frame 12 and a polysilicon layer 14 attached to one side of the frame 12. Located within the boundaries of the polysilicon layer 14 are two polysilicon plates 16 which are located in openings 18 in the polysilicon layer 14. Each of the two polysilicon plates 16 contain two platinum thin film resistors (not shown), one forming a heater with heater terminals 20 and the other forming a temperature sensing detector (RTD). One of the polysilicon plates 16, the sensing element, has a catalytic layer deposited thereon, while the other, the reference element, (having no catalyst deposited thereon) is used for temperature compensation. When combustibles are present in a gas sample, the exothermic reactions of these molecules on the catalytic layer raises the temperature of the sensing element above that of the reference element. A measurement of the temperature difference between the two elements by means of the two RTDs provides a measure of the concentration of the combustibles in the gas sample. It should be appreciated that the calorimetric gas sensor 11 is conventional and known in the art.

The apparatus 10, according to the present invention, includes a cap or enclosure 24 disposed partially over the calorimetric gas sensor 11. Preferably, the enclosure 24 encloses the sensing element and the reference element. The enclosure 24 can be rectangular in shape and can be fabricated from bulk silicon etching a cavity from one side to make a hollow frame 26. The enclosure 24 has a p+ type silicon layer 28 attached to a top side of the frame 26. The enclosure 24 has at least one aperture 30 extending through the layer 28 to allow combustibles to contact the sensing element and reference element of the calorimetric gas sensor 11. It should be appreciated that the aperture 30 may have any suitable shape.

In one embodiment, the apparatus 10 includes a cantilever beam 32 formed by etching the p+ type silicon layer using micromachining procedures which are conventional and known in the art. The beam 32 can be of rectangular shape or a more complex shape or geometry, such as that of a paddle attached by means of a narrow end short arm. It should be appreciated that since the beam 32 is etched in the layer 28, the open space 34 is defined in part by the shape of the beam 32, but the area of the opening can be kept much smaller than the area of the cantilever beam 32 so that most of the aperture 30 is blocked. It should also be appreciated that the cantilever beam 32 may be made from a layer placed on top of the layer 28. For such a case, the beam 32 can either completely cover the aperture 30 or partially cover the aperture 30 such that an open space 34 exists between the cantilever beam 32 and the remaining top portion of the enclosure 24.

The cantilever beam 32 is a bimorph structure. The lower part of the cantilever beam 32 is covered with a layer 36 of a metal such as nickel that has a much larger temperature expansion coefficient than that of silicon. The cantilever beam 32 also includes a resistor 38 embedded on the top of the beam 32. The resistor 38 is a very thin metal patterned as a heater. It should be appreciated that the resistor 38 is connected to a source of electrical power (not shown).

In operation, the flux of combustibles reacting with oxygen (e.g., CO, HC) of a gas entering the enclosure 24 is modulated at a predetermined frequency omega ($\omega$) by periodically restricting the aperture 30 with the cantilever beam 32. It should be appreciated that for on-board exhaust gas detection, $\omega$ can be five (5) to ten (10) Hertz. Since the cantilever beam 32 has a low mass, it rapidly heats when power is applied to the resistor 38 and rapidly cools when the power is turned off, thus it can oscillate rapidly. Thus, the modulation of the flux of reactants or combustibles reacting with oxygen entering the enclosure 24 can be modulated at a predetermined frequency $\omega$ (for instance 20 Hz) by an alternating current (AC) signal of frequency $\omega/2$ applied to the resistor 38. If the flux of combustibles being oxidized on the catalyst of the sensing element is comparable to the maximum flux entering the cavity through the aperture, then, the sensor output is modulated at the same frequency $\omega$ at which the beam periodically restricts the aperture. If the sensor signal output is measured at this frequency $\omega$, most of the noise outside this frequency is eliminated. In addition, this AC signal largely eliminates the DC zero-offset drift which limits the accuracy of the calorimetric gas sensor 11.

Figure 3:
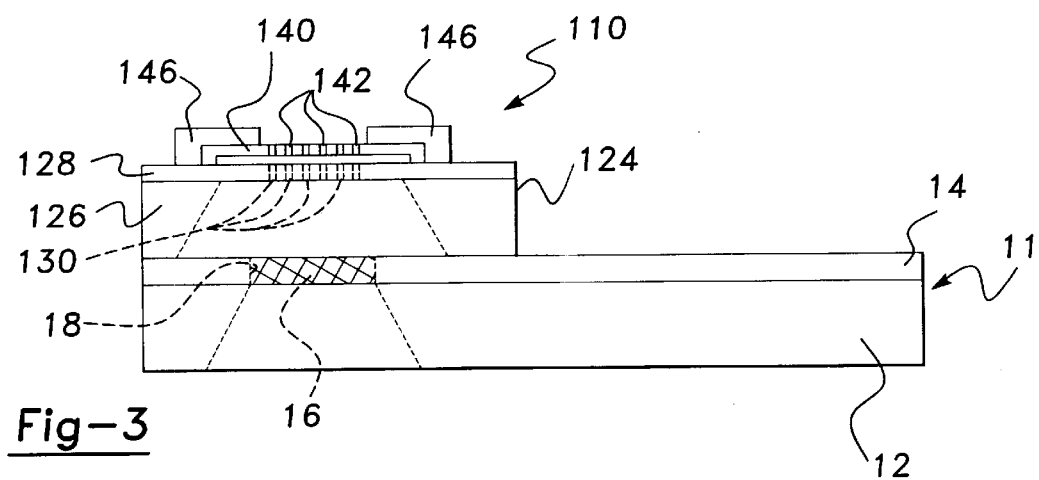
FIG. 3 is a cross-sectional elevational view of another apparatus, according to the present invention, illustrated in operational relationship with a calorimetric gas sensor.
Figure 4:
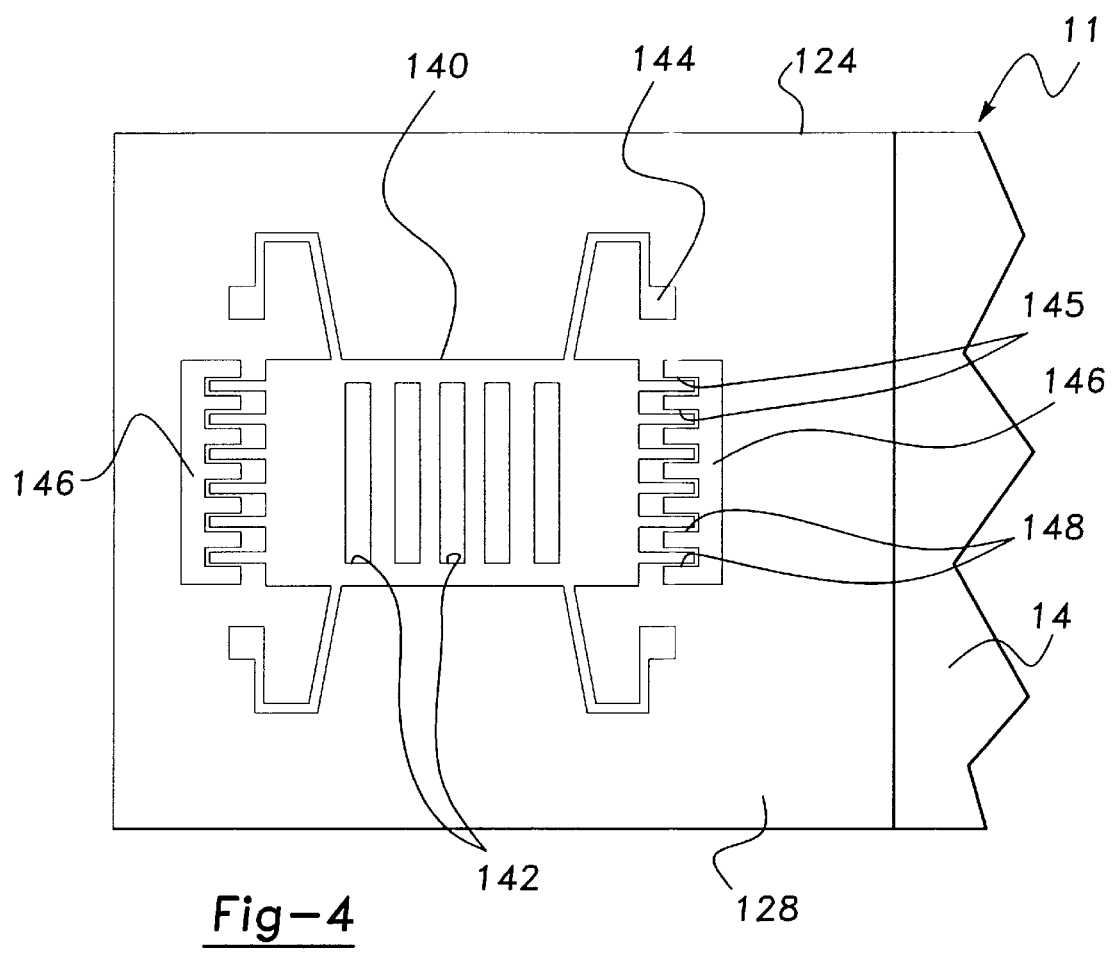
FIG. 4 is a top view of the apparatus and calorimetric gas sensor of FIG. 3.

Referring to FIGS. 3 and 4, another embodiment 110 of the apparatus 10 is shown. Like parts of the apparatus 10 have like reference numerals increased by one hundred (100). The apparatus 110 includes a cap or enclosure 124 disposed partially over the calorimetric gas sensor 11. Preferably, the enclosure 124 encloses the sensing element and the reference element. The enclosure 124 can be rectangular in shape and can be fabricated from bulk silicon etching a cavity from one side to make a hollow frame 126.

The enclosure 124 has a p+ type silicon layer 128 attached to a top side of the frame 126. The enclosure 124 has at least one, preferably a plurality of slots or apertures 130 extending through the layer 128 to allow combustibles to contact the sensing element and reference element of the calorimetric gas sensor 11. The apertures 130 are generally rectangular in shape, extending transversely and spaced longitudinally along the layer 128. It should be appreciated that the apertures 130 may have any suitable shape.

In this embodiment, the apparatus 110 includes a shutter 140 to open and close the apertures 130. The shutter 140 is fabricated using polysilicon and conventional surface micromachining techniques. The shutter 140 has, at least one, preferably a series of apertures 142 extending therethrough transversely and spaced longitudinally in registry with the apertures 130 in the layer 128 of the enclosure 124.

The shutter 140 is suspended above the enclosure 124 by means of four flexible arms 144 that allow the shutter 140 to slide easily along a plane defined by the top of the enclosure 124. The shutter 140 includes a series of teeth 145 at either end, each matching a comb structure 146 rigidly anchored on layer 128 and having a plurality of recesses 148 to receive the teeth 145. Each comb structure 146 and teeth 145 pair form an interdigitated comb drive. By electrostatic attraction, interdigitated comb structures 146 make the shutter 140 oscillate longitudinally in either direction to modulate the apertures 130 of the enclosure 124.

In operation, the flux of combustibles reacting with oxygen entering the enclosure 124 is modulated at a predetermined frequency omega ($\omega$) by periodically restricting the apertures 130 with the shutter plate 140. The shutter plate 140 oscillates along the top of the enclosure 124 by applying an AC signal to the comb drives 146 to modulate the flux of the combustibles entering the enclosure 124. The width of the apertures 142 can be made equivalent to the length of the travel achievable with the comb drives 146, which can be several micrometers. Since the shutter plate 140 needs to be raised by only 0.3 to 0.5 micrometers over the layer 128 to avoid friction, the shutter 140 provides a substantial restriction for the apertures 130. It should be appreciated that for on-board exhaust gas detection, $\omega$ can be five (5) to ten (10) Hertz.

Additionally, a method, according to the present invention, is provided for modulating flux of combustibles reacting with oxygen impinging on the calorimetric gas sensor 11. The method includes the step of enclosing the sensing element and the reference element of the calorimetric gas sensor 11 with the apparatus 10,110 having at least one aperture 30,130 to allow combustibles to enter and impinge on the sensing element and the reference element. The method also includes the step of periodically restricting the aperture 30,130 of the apparatus 10,110 to modulate the flux of combustibles entering at a predetermined frequency to produce an AC output signal from the calorimetric gas sensor 11 and measuring the sensor output at the frequency at which the aperture is restricted.

The present invention has been described in an illustrative manner. It is to be understood that the terminology which has been used is intended to be in the nature of word of description rather than of limitation.

Many modifications and variations of the present invention are possible in light of the above teachings. Therefore, within the scope of the appended claims, the present invention may be practiced other than as specifically described.

What is claimed is:

1. A method for modulating flux of combustibles reacting with oxygen impinging on a calorimetric gas sensor, said method comprising the steps of:

enclosing a sensor comprising a sensing element and a reference element of a calorimetric gas sensor with an apparatus having at least one aperture to allow combustibles to enter and impinge on the sensing element and reference element;

periodically restricting the aperture of the apparatus to expose solely the combustibles to the calorimetric gas sensor and to modulate the flux of combustibles solely entering at a predetermined frequency to produce an AC output signal from the calorimetric gas sensor; and measuring the sensor output at the frequency at which the aperture is restricted.

2. A method as set forth in claim 1 including the step of providing an enclosure having a hollow bulk silicon frame and a p+ type silicon layer on top of the frame with the at least one aperture extending through the layer for the apparatus.

3. A method as set forth in claim 2 including the step of providing a shutter plate on the enclosure for the apparatus to at least partially restrict the aperture.

4. A method as set forth in claim 3 wherein the shutter plate is made of polysilicon and suspended above the layer.

5. A method for modulating flux of combustibles reacting with oxygen impinging on a calorimetric gas sensor, said method comprising the steps of:

enclosing a sensor comprising a sensing element and a reference element of a calorimetric gas sensor with an apparatus having at least one aperture to allow combustibles to enter and impinge on the sensing element and reference element;

periodically restricting the aperture of the apparatus to modulate the flux of combustibles entering at a predetermined frequency to produce an AC output signal from the calorimetric gas sensor;

measuring the sensor output at the frequency at which the aperture is restricted;

providing an enclosure having a hollow bulk silicon frame and a p+ type silicon layer on top of the frame with the at least one aperture extending through the layer for the apparatus; and providing a cantilever beam on the enclosure for the apparatus to at least partially restrict the aperture.

6. A method as set forth in claim 5 wherein the beam is a bimorph structure.

7. A method as set forth in claim 6 including the step of providing a heater about the beam to move the beam to open and restrict the aperture.

8. A method as set forth in claim 7 including the step of applying an AC signal to the heater to modulate the beam.

9. A method for modulating flux of combustibles reacting with oxygen impinging on a calorimetric gas sensor, said method comprising the steps of:

enclosing a sensor comprising a sensing element and a reference element of a calorimetric gas sensor with an apparatus having at least one aperture to allow combustibles to enter and impinge on the sensing element and reference element;

periodically restricting the aperture of the apparatus to modulate the flux of combustibles entering at a predetermined frequency to produce an AC output signal from the calorimetric gas sensor;

measuring the sensor output at the frequency at which the aperture is restricted;

providing an enclosure having a hollow bulk silicon frame and a p+ type silicon layer on top of the frame with the at least one aperture extending through the layer for the apparatus;

providing a shutter plate on the enclosure for the apparatus to at least partially restrict the aperture, wherein the shutter plate is made of polysilicon and suspended above the layer; and providing at least one comb device to electrostatically actuate and move the shutter plate to open and restrict the aperture.

10. A method as set forth in claim 9 including the step of apply an AC signal to the comb drive to modulate the shutter plate.

11. An apparatus for modulating flux of combustibles reacting with oxygen impinging on a calorimetric gas sensor comprising:

an enclosure enclosing a sensor comprising a sensing element and a reference element of a calorimetric gas sensor, said enclosure having at least one aperture and a single cavity to allow combustibles to enter and impinge on the sensing element and the reference element;

a structure means for periodically restricting the aperture of said enclosure to modulate the flux of combustibles entering at a predetermined frequency to produce an AC output signal from the calorimetric gas sensor; and an electronic circuit to measure the sensor output at the frequency at which the aperture is restricted.

12. An apparatus as set forth in claim 11 wherein said enclosure has a hollow bulk silicon frame and a p+ type silicon layer on top of said frame with said at least one aperture extending through said layer.

13. An apparatus as set forth in claim 11 including a shutter plate on said enclosure to at least partially restrict said at least one aperture.

14. An apparatus as set forth in claim 13 wherein said shutter plate is made of polysilicon and suspended above said layer.

15. An apparatus for modulating flux of combustibles reacting with oxygen impinging on a calorimetric gas sensor comprising:

an enclosure enclosing a sensor comprising a sensing element and a reference element of a calorimetric gas sensor, said enclosure having at least one aperture to allow combustibles to enter and impinge on the sensing element and the reference element;

a structure for periodically restricting the aperture of said enclosure to modulate the flux of combustibles entering at a predetermined frequency to produce an AC output signal from the calorimetric gas sensor;

an electronic circuit to measure the sensor output at the frequency at which the aperture is restricted;

said enclosure having a hollow bulk silicon frame and a p+ type silicon layer on top of said frame with said at least one aperture extending through said layer; and a cantilever beam on said enclosure to at least partially restrict said at least one aperture.

16. An apparatus as set forth in claim 15 wherein said beam is a bimorph structure.

17. An apparatus as set forth in claim 16 including a heater about said beam to move said beam to open and restrict said at least one aperture.

18. An apparatus for modulating flux of combustibles reacting with oxygen impinging on a calorimetric gas sensor comprising:

an enclosure enclosing a sensor comprising a sensing element and a reference element of a calorimetric gas sensor, said enclosure having at least one aperture to allow combustibles to enter and impinge on the sensing element and the reference element;

a structure for periodically restricting the aperture of said enclosure to modulate the flux of combustibles entering at a predetermined frequency to produce an AC output signal from the calorimetric gas sensor;

an electronic circuit to measure the sensor output at the frequency at which the aperture is restricted;

a shutter plate on said enclosure to at least partially restrict said at least one aperture, said shutter plate being made of polysilicon and suspended above said layer; and at least one comb device to electrostatically actuate and move said shutter plate to open and restrict said at least one aperture.

19. An apparatus as set forth in claim 18 wherein said shutter plate includes at least one second aperture extending therethrough for registry with said at least one aperture.

20. An apparatus for modulating flux of combustibles reacting with oxygen impinging on a calorimetric gas sensor comprising:

an enclosure enclosing a sensor comprising a sensing element and a reference element of a calorimetric gas sensor, said enclosure having at least one aperture and a single cavity to allow combustibles to enter and impinge on the sensing element and the reference element;

means on said enclosure for periodically restricting said at least one aperture of said enclosure to modulate the flux of combustibles entering at a predetermined frequency to produce an AC output signal from the calorimetric gas sensor; and means for measuring the sensor output at the frequency at which said at least one aperture is restricted.

* * * * *